US00PP12548P2

(12) United States Plant Patent
Lamb et al.

(10) Patent No.: US PP12,548 P2
(45) Date of Patent: Apr. 16, 2002

(54) SPATHIPHYLLUM PLANT NAMED 'SOPHIA'

(75) Inventors: Ann E. Lamb, Sebring; David R. Lilly, Boynton Beach; Randy L. Allamand, Lake Placid, all of FL (US)

(73) Assignee: Twyford Palnt Laboratories, Inc., Sebring, FL (US)

( * ) Notice: Subject to any disclaimer, the term of this patent is extended or adjusted under 35 U.S.C. 154(b) by 0 days.

(21) Appl. No.: 09/661,648

(22) Filed: Sep. 13, 2000

(51) Int. Cl.[7] ..... A01H 5/00
(52) U.S. Cl. ..... Plt./364
(58) Field of Search ..... Plt./364

*Primary Examiner*—Bruce R. Campell
*Assistant Examiner*—Annette H. Para
(74) *Attorney, Agent, or Firm*—Foley & Lardner

(57) ABSTRACT

A new Spathiphyllum plant named 'Sophia' characterized by its intermediate stature, dense branching, and its ovate white spathes held just above the foliage. The foliage of 'Sophia' is shiny and textured, with distinctive wavy margins. Plants of 'Sophia' is shiny and textured, with distinctive wavy margins. Plants of 'Sophia' grow quickly to marketable size, bloom and re-bloom quickly, and are adaptable to a variety of pots sizes from 15 cm through 25 cm. Plants of 'Sophia' are also well adapted to indoor conditions. These combined characteristics make 'Sophia' a unique new cultivar.

4 Drawing Sheets

BACKGROUND OF THE INVENTION

The present invention comprises a new and distinct cultivar of Spathiphyllum plant, botanically known as *Spathiphyllum hybrid*, and referred to by the cultivar name 'Sophia'.

The new cultivar is the product of a breeding program carried out by the inventors, Ann E. Lamb, David R. Lilly, and Randy L. Allamand. The new cultivar named 'Sophia' is the result of a cross made in Apopka, Fla. in November of 1993. The female or seed parent is Spathiphyllum 'Petite' (unpatented). The male parent is a selection Spathiphyllum Mauna Loa 'Linda' (unpatented) selected and maintained by the inventors, and used only for breeding purposes.

The new cultivar named 'Sophia' was discovered and selected by the inventors from a group seedlings of the stated cross in Homestead Fla. on Feb. 26, 1996. Propagation by tissue culture in the laboratories of Twyford Plant Laboratories, Inc. under the supervision of the inventors, was used to increase the number of plants for evaluation, and has demonstrated the stability of the combination of characteristics as herein described from generation to generation, are firmly fixed and reproduces true to type.

BRIEF DESCRIPTION OF THE INVENTION

The following traits have been repeatedly observed and are determined to be basic characteristics of 'Sophia' which in combination distinguish this Spathiphyllum as a new and distinct culvar:

1. Plants of 'Sophia' have an intermediate growth habit, and are ideally suited for 15 cm thru 25 cm pots.
2. The leaves of 'Sophia' are dark green, shiny, textured, and have a wavy margin.
3. Plants of 'Sophia' naturally bloom early, abundantly, repeatedly, and year-round.
4. Plants of 'Sophia' are very dense, leafy and very well branched.
5. Plants of 'Sophia' grow very quickly and vigorously.

6. Plants of 'Sophia' are particularly well adapted to indoor conditions,

'Sophia' has not been observed under all possible environmental conditions. The phenotype of the new cultivar may vary significantly with variations in environment such as temperature, light intensity, and day length, without any change in genotype.

Of the commercial cultivars known to the present inventors, the most similar in comparison to 'Sophia' is the cultivar 'Viscount' (unpatented). In comparison to 'Viscount', 'Sophia' is faster growing and more highly branched. Plants of 'Sophia' bloom earlier than 'Viscount', more abundantly, and year-round. The new cultivar 'Sophia' can also be compared to the new cultivar named 'Connie' (U.S. Plant patent application Ser. No. 09/238,730). The new cultivars 'Sophia' and 'Connie' were selected from the same cross. The new cultivar named 'Sophia' is similar to 'Connie' with respect to features such as growth rate, flowering, and general appearance. However, 'Sophia' differs from 'Connie' because plants of 'Sophia' grow taller, have wider leaves and produce spathes which open closer to the top of the leaf canopy.

In comparison to the parental cultivars, Spathiphyllum 'Sophia' is intermediate in growth habit, between 'Petite' and 'Linda'.

Spathiphyllum 'Petite' is a small plant. It is grown in 4"–6" pots. Spathiphyllum 'Linda' is a large, upright growing variety used in 10"–14" pots, with broad dark green leaves and large bright white spathes held above the foliage.

The leaves of 'Sophia' are intermediate in size and width between those of 'Petite' and 'Linda'. The leaves of 'Sophia' are considerably more textured than those of 'Petite'. Plants of 'Sophia' are more floriferous than either parent.

BRIEF DESCRIPTION OF THE DRAWING

The accompanying color photographic illustrations show typical characteristics of a 14-month old plant of 'Sophia' grown in a 25 cm pot initiated from three microcuttings obtained by tissue culture and grown under appropriate growing conditions, with colors being as nearly true as possible with illustrations of this type.

Sheet 1 is a side view showing the inflorescence and foliage of a plant of 'Sophia'.

Sheet 2 is a close-up view of the inflorescence of the instant plant.

Sheet 3 shows the detail of the upper leaf surface.

Sheet 4 shows the detail of the lower leaf surface.

DETAILED BOTANICAL DESCRIPTION

The following observations, measurements and values describe plants grown in Homestead, Fla., were 14 months old (3 month old liner+11 months finish time), were finished in 25 cm pots under greenhouse conditions which closely approximate those generally used in horticultural practice. All color references are measured against The Royal Horticultural Society (R.H.S.) Colour Chart. Colors are approximate as color depends on horticultural practices such as light level and fertilization rate, among other, without, however, any variance in genotype.

Classification:

*Commercial.*—*Spathiphyllum hybrid* cv. 'Sophia'.

Parentage:

*Male parent.*—Spathiphyllum 'Petite'.

*Female parent.*—Selection of Spathiphyllum 'Mauna Loa'/'Linda'.

Propagation: Vegetative, by tissue culture.

Plant: Under appropriate growing conditions, Sophia as depicted in Sheet 1 attains a size of approximately 60 cm to 68 cm in height, as measured from the top of the soil to the top of the leaf canopy, and approximately 100 cm to 110 cm in width.

Leaves:

*Form.*—The leaf blade is ovate with an acuminate apex and an obtuse to cunate base. The margins are entire and distinctly wavy. The midrib tends to curve over the length of the leaf. The leaf blade is typically curved downward at the tip. The leaf surface is textured and shiny.

*Size.*—Leaf blades are approximately 28 cm to 34 cm in length and approximately 12.4 cm to 15.2 cm in width.

*Petiole.*—The petiole is approximately 35 cm to 41 cm in length from the base of the petiole to the base of the leaf blade on the primary shoot. Secondary shoots are smaller depending on the age of the shoot. The petiole is approximately 6 mm to 8 mm in diameter at the junction of the geniculum and petiole sheath. There is one straight petiole below the geniculum.

*Petiole sheath.*—The petiole sheath is approximately 29 cm to 33.5 cm in length and approximately 9 mm to 12 mm in width at midpoint. The tip of the petiole sheath tapers and becomes flush with the petiole.

*Geniculum.*—The geniculum is approximately 4 cm to 5 cm in length, approximately 6 mm to 8 mm in diameter. The color is RHS 146 B.

*Veins.*—Veins are sunken, and the leaf blade convex between veins on the upper surface giving the leaf a textured appearance. The midrib is sunken. Well defined primary veins radiate out from the midrib over the length of the leaf. There are approximately 14 pairs of primary veins on the leaf.

*Color.*—Leaf: Upper surface: Greener than, but closest to RHS 139 A. Lower surface: Darker, and greener than, but closest to RHS 147 B. Midrib: Upper surface: Greener than but closest to RHS 139 A. Lower surface: Between RHS 145 C and RHS 146 D. Petiole: Darker and greener than, but closest to RHS 137 A. Petiole sheath: Darker and greener than, but closest to RHS 137 A.

Roots: Thick White roots with fine laterals.

INFLORESCENCE

Immature: The spathe is tightly rolled around the spadix and emerges from the petiole sheath. The spathe is fully open approximately when the peduncle is fully elongated. The inflorescence is approximately 69 cm to 78 cm in height measured from the soil surface to the apex of the spathe. The peduncle is approximately 56 cm to 63 cm in height measured from its base to the base of the spathe, and approximately 5 mm to 6 mm in diameter measured at its midpoint. The color of the peduncle is greener than, but closest to between RHS 137 A and RHS 137 B.

Mature:

*Spathe.*—Size: The spathe is approximately 14 cm to 16 cm long and approximately 7.5 cm to 8.6 cm in width. It is cupped, approximately 3 cm in depth. Shape: Cupped, ovate, with cuneate base and twisted acuminate apex. Margin: Smooth to slightly wavy, enitre.

*Color.*—Fully open: Adaxial surface: Pure white RHS 155 D. Abaxial surface: Pure white RHS 155 D. Apex: RHS 146 C (back); RHS 155 D tinged with RHS 146 C (front). Midrib: RHS 146 b.

*Faded.*—Adaxial surface: RHS 155 D streaked with RHS 146 B. Abaxial surface: RHS 155 D streaked with RHS 146 A. Apex: Between RHS 146 A and RHS 146 B (back), tinged with RHS 146 B (front). Midrib: Between RHS 146 A and RHS 146 B.

*Arrangement.*—The spathe terminates as a straight peduncle which opens vertically above the leaves.

*Shape.*—The spathe is ovate with a cuneate base and a twisted acuminate apex.

*Flowering.*—Depending on season, approximately 4 to 8 blossoms will be present on plants as illustrated in Sheet 1 and described in this text. Smaller narrower blossoms may occur on less mature growth.

*Lastingness of the inflorescence.*—Spathes begin to change from white to green after about 3–4 weeks, becoming almost entirely green after about 6 weeks. Cut flowers last about 7 days off the plant.

*Fragrance.*—Flowers moderately fragrant, particularly late morning, through mid afternood.

REPRODUCTIVE ORGANS

Spadix:

*Size.*—Approximately 8.1 cm to 9.2 cm in height and approximately 1.4 cm to 1.7 cm in width.

*Color.*≦When the spathe unrolls, the spadix is 19 C gradually changing to green between RHS 146 B and RHS 146 C as the flower fades.

*Stamens.*—Anthers and filaments are minute and not clearly visible.

*Pollen.*—White.

*Pistil.*—Translucent white in color, conical, protruding between the staminate flowers, fixed to the main axil. The pistillate flowers extend approximately 3 mm beyond the staminate flowers.

*Seeds.*—Approximately 2 mm in length, reniform in shape, light to medium brown, with pitted texture. Each individual capsule contains about 1–6 seeds. Depending on size and degree of pollination, a single inflorescence can yield over 500 seeds.

*Fruit.*—Oblong to elliptic berry, 6 mm long, 5–6 mm wide, darker than, but closest to green RHS 147 A, becoming tinged with yellow RHS 19 A, RHS 19 B when ripe.

*Disease/pest resistance/susceptibility.*—Preventative disease and pest control measures used to grow crops of 'Sophia' are typical of ordinary common practice. 'Sophia' has no particular sensitivity to common pests or pathogens. By comparison, 'Sophia' is more resistant to disease than its parents 'Petite' and 'Linda'. Otherwise, it is similar to 'Viscount' in disease resistance.

We claim:

1. A new and distinct cultivar of Spathiphylluin plant named 'Sophia', as illustrated and described.

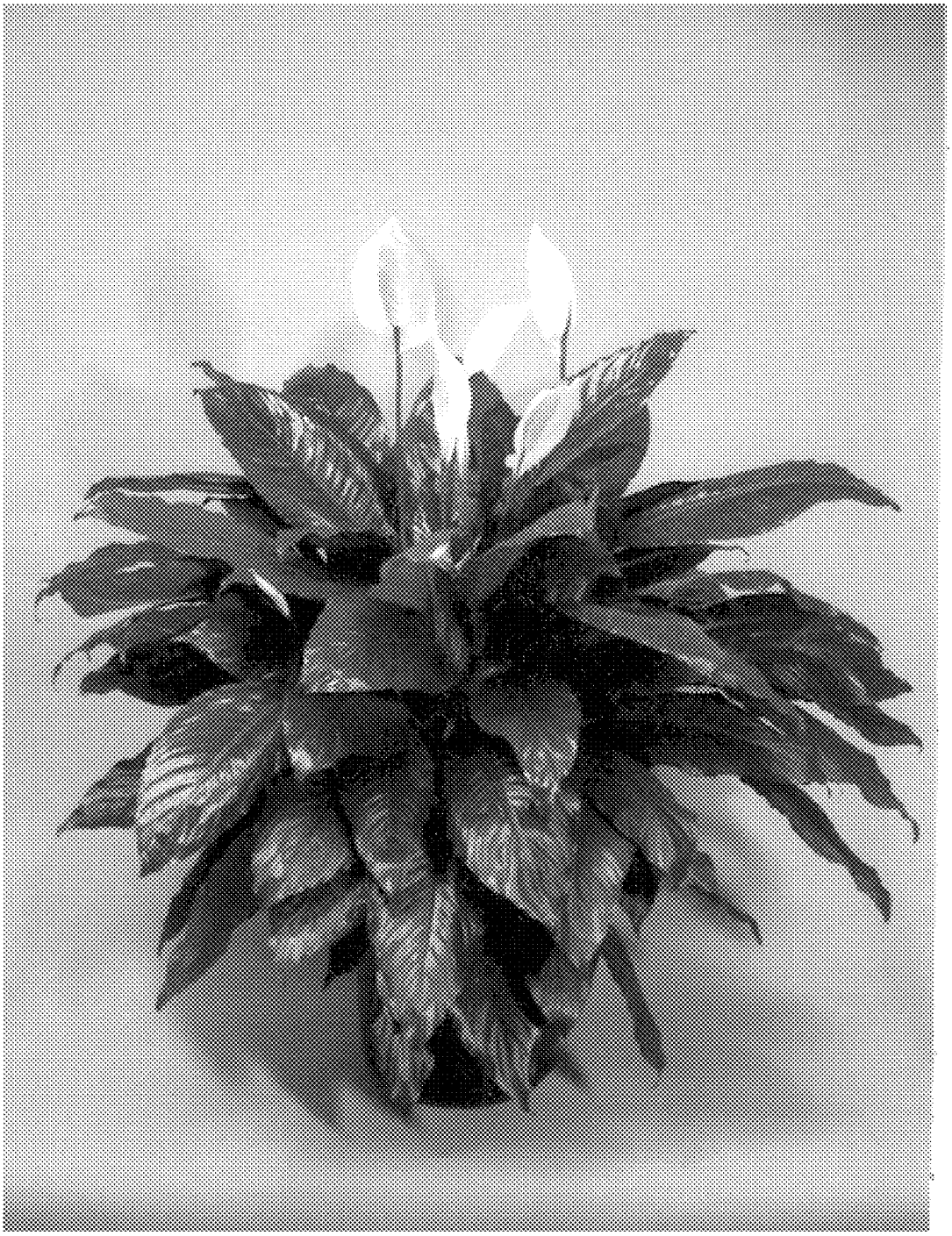

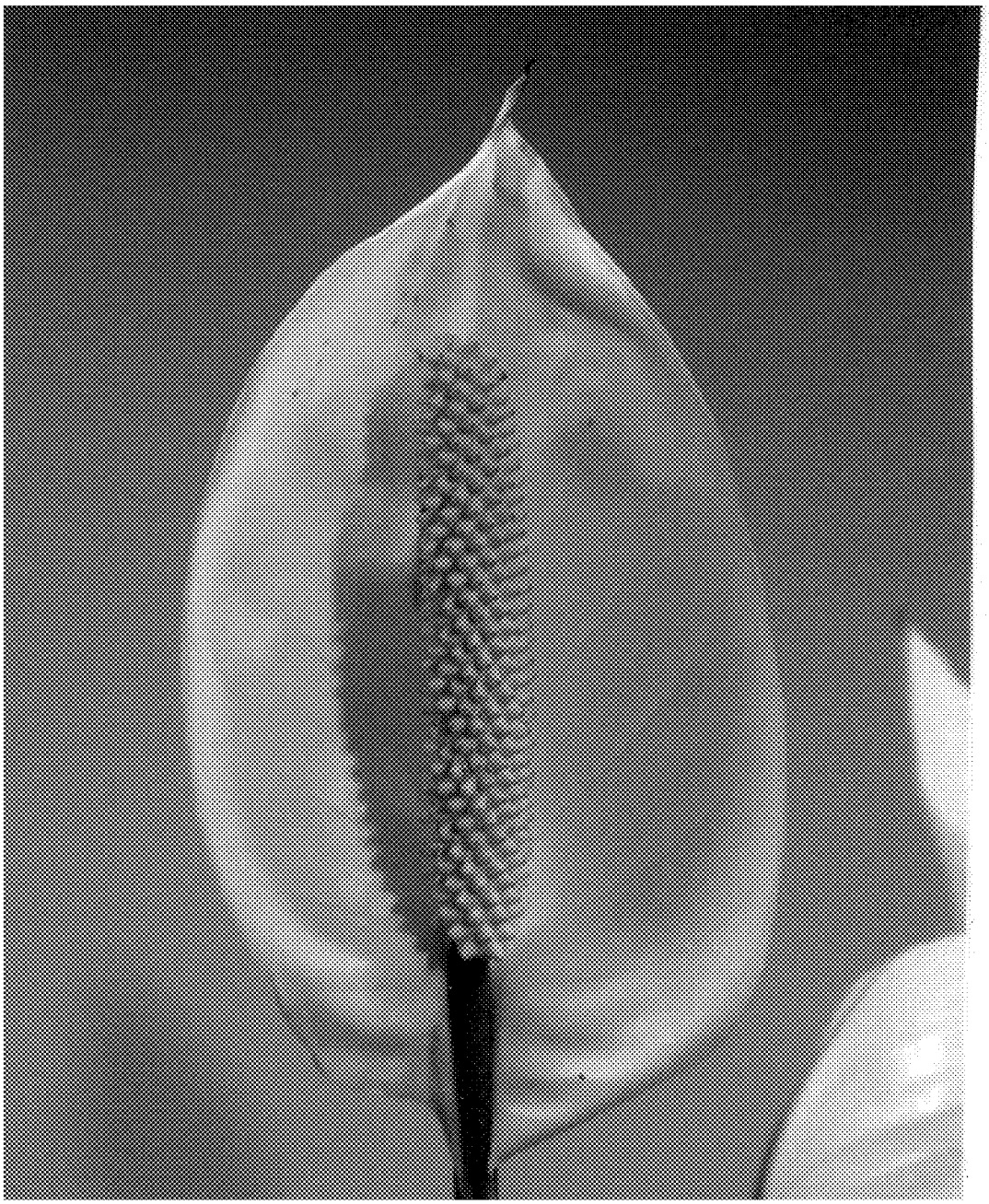

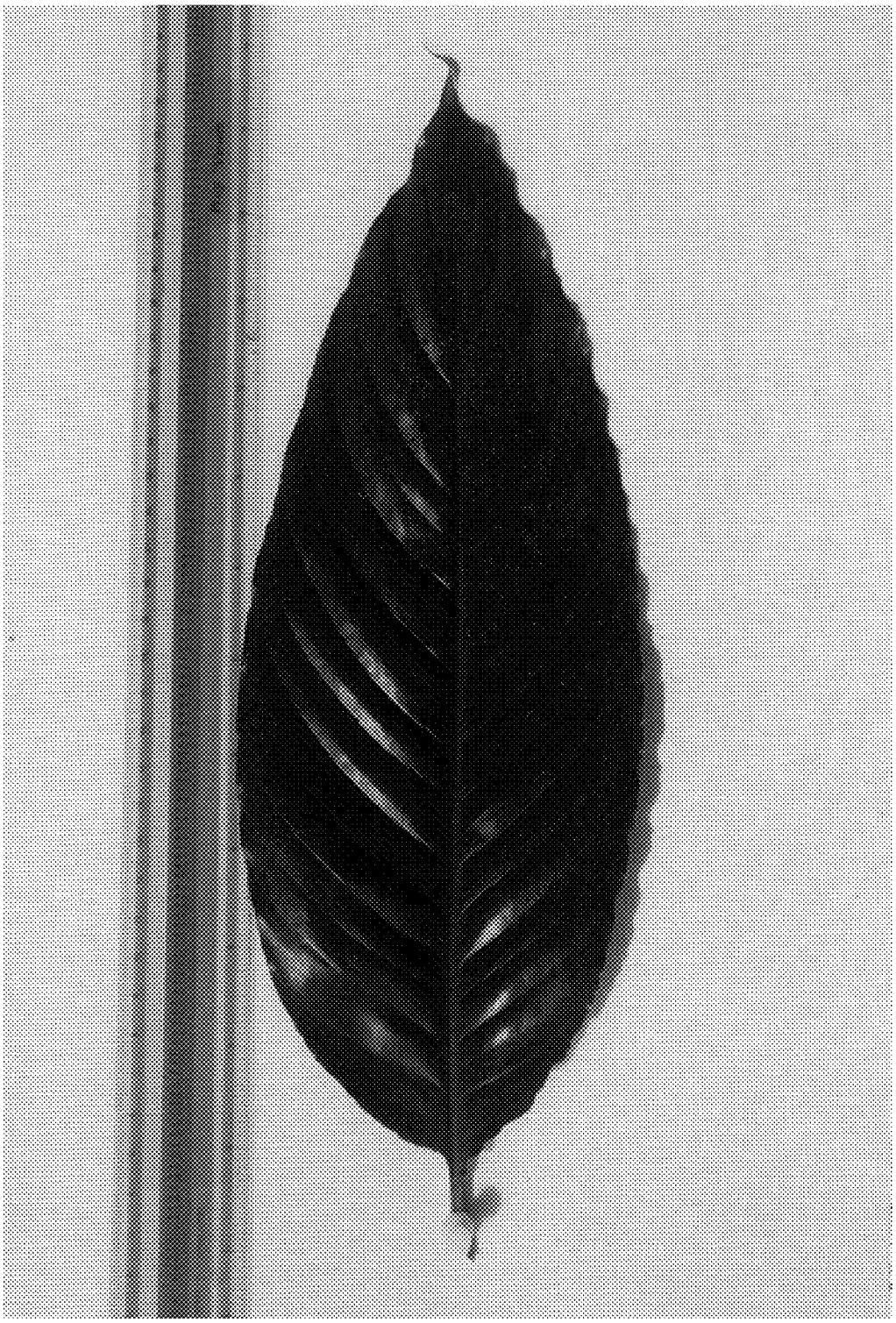

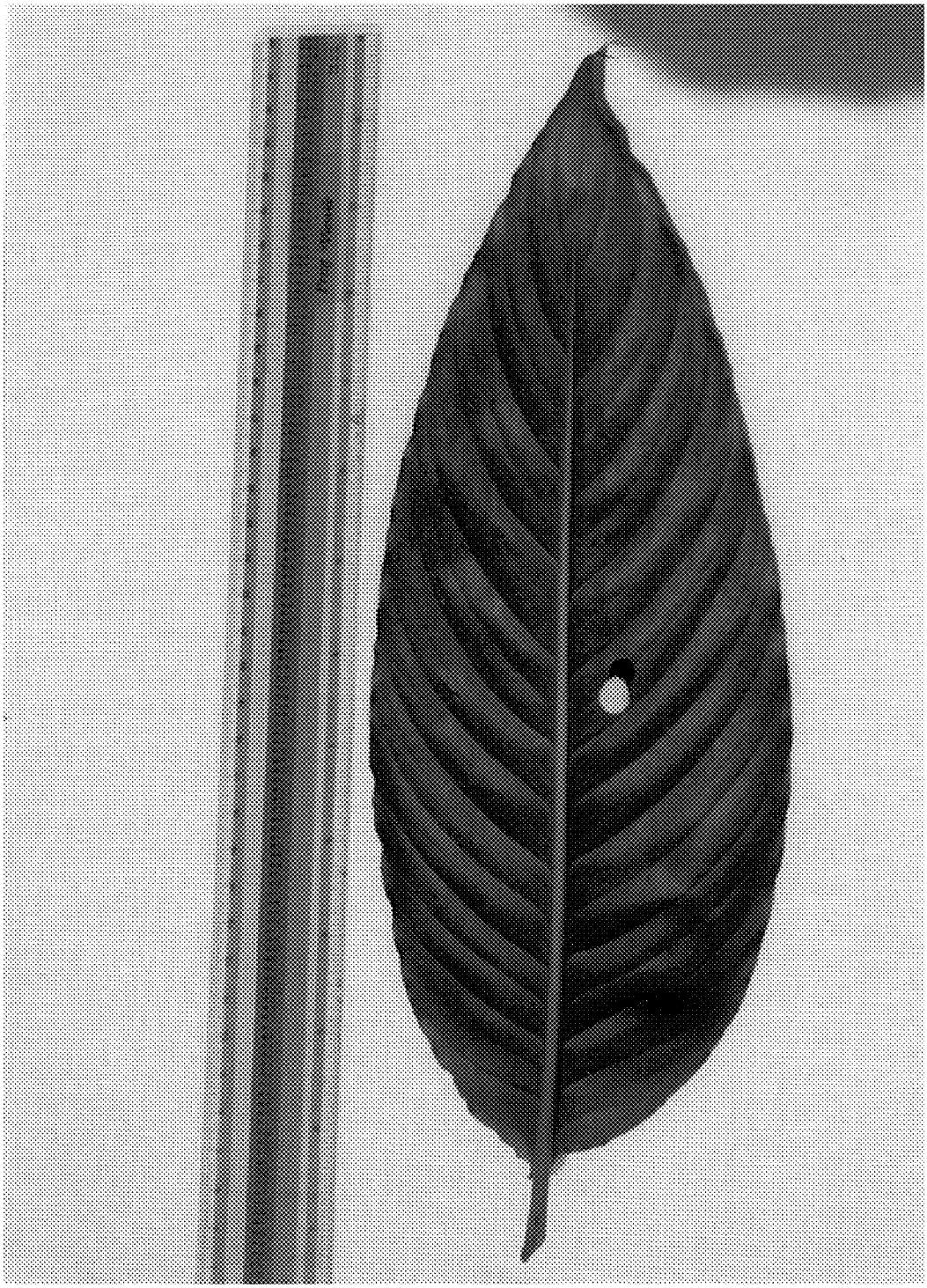

* * * * *